United States Patent [19]

Sarantakis

[11] 4,011,207
[45] Mar. 8, 1977

[54] DES-(ALA¹, GLY²,LYS⁴-SRIF, DES-(ALA¹, GLY², LYS⁴)-D-TRP⁸-SRIF AND INTERMEDIATES

[75] Inventor: Dimitrios Sarantakis, West Chester, Pa.

[73] Assignee: American Home Products Corporation, New York, N.Y.

[22] Filed: Mar. 8, 1976

[21] Appl. No.: 664,608

Related U.S. Application Data

[63] Continuation-in-part of Ser. No. 537,037, Dec. 27, 1974, abandoned.

[52] U.S. Cl. .................. 260/112.5 S; 424/177
[51] Int. Cl.² ............... C07C 103/52; A61K 37/00
[58] Field of Search ............ 260/112.5 S; 424/177

[56] References Cited

UNITED STATES PATENTS 3,933,784   1/1976   Sarantakis ................ 260/112.5

Primary Examiner—Lewis Gotts
Assistant Examiner—Reginald J. Suyat
Attorney, Agent, or Firm—Richard K. Jackson

[57] ABSTRACT

The undecapeptide H-Cys-Asn-Phe-Phe-Trp-Lys-Thr-Phe-Thr-Ser-Cys-OH, its D-Trp⁸ analogue, their oxidized forms and intermediates obtained in their synthesis are described. These undecapeptides inhibit the secretion of the hormone somatotropin (growth hormone).

8 Claims, No Drawings

DES-(ALA¹, GLY²,LYS⁴-SRIF, DES-(ALA¹, GLY², LYS⁴)-D-TRP⁸-SRIF AND INTERMEDIATES

RELATED APPLICATIONS

This application is a continuation-in-part of Ser. No. 537,037, filed December 27, 1974, now abandoned.

DESCRIPTION OF THE INVENTION

This invention relates to novel undecapeptides and intermediates obtained in their synthesis by classical and solid phase methods of peptide synthesis.

Somatostatin (also known as somatotropin release inhibiting factor or SRIF) is the tetradecapeptide H—Ala—Gly—Cys—Lys—Asn—Phe—Phe—Trp—Lys—Thr—Phe—Thr—Ser—Cys—OH. This tetradecapeptide has only recently been identified by isolation from extracts of ovine hypothalamic tissues and found to inhibit the secretion of the hormone somatotropin which is commonly referred to as the growth hormone (GH); See Brazeau et al., Science, 179 pp. 77–79 (January 1973). The linear form of this tetradecapeptide, H-Ala-Gly-Cys-Lys-Asn-Phe-Phe-Trp-Lys-Thr-Phe-Thr-Ser-Cys-OH, has also been reported by Brazeau et al., supra, to have been synthesized by solid phase methodology and found to have the same biological activity as the somatostatin obtained from a natural source. In U.S. Pat. No. 3,882,098 the undecapeptide Des-Ala¹-Gly²-Asn⁵-SRIF and its oxidized form are described and in copending application Ser. No. 457,038 filed Apr. 1, 1974, the dodecapeptide Des-Ala¹-Gly²-SRIF and its oxidized form are described.

The novel undecapeptides of the present invention are analogs of somatostatin and the linear counterpart of somatostatin in which the amino acids in the one, two and four positions of somatostatin have been omitted and the tryptophyl moiety in 8-position is either in the L or the D configuration.

The undecapeptides of the present invention which inhibit the secretion of the hormone somatotropin is represented by the formula:

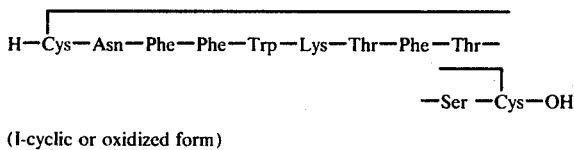

(I-cyclic or oxidized form)

in which Trp represents L-tryptophyl or D-tryptophyl, all other chiral amino acid residues being in the L-configuration and the non-toxic acid addition salts thereof. Illustrative of acid addition salts are hydrochloride, hydrobromide, sulfate, phosphate, maleate, acetate, citrate, benzoate, succinate, malate, ascorbate and the like.

The nomenclature used to depict the peptides follows that adopted by Schroder & Lubke, "The Peptides," 1, pp viii-xxix (Academic Press 1965). All chiral amino acid residues containing a chiral carbon atom identified in formula I and the other formulas hereinafter are of the natural or L-configuration unless specified otherwise.

The present invention also relates to novel undecapeptides intermediates of the formulas:

H—Cys—Asn—Phe—Phe—Trp—Lys—Thr—Phe—Thr—Ser—Cys—OH (II-linear form)

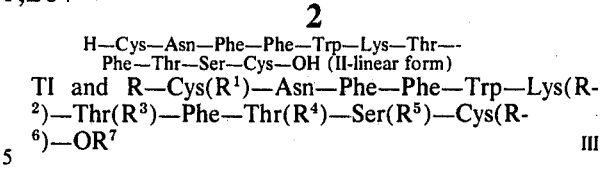

wherein:

Trp is L-typtonphyl or D-tryptophyl;

R is either hydrogen or an α-amino protecting group. The α-amino protecting groups contemplated by R are those known to be useful in the art in the step-wise synthesis of polypeptides. Among the classes of α-amino protecting groups covered by R are (1) acyl type protecting groups illustrated by the following: formyl, trifluoroacetyl, phthalyl, toluenesulfonyl (tolsyl), benzenesulfonyl, nitrophenylsulfenyl, tritylsulfenyl, o-nitrophenoxyacetyl, chloroacetyl, acetyl, γ-chlorobutyryl, etc.; (2) aromatic urethan type protecting groups illustrated by benzyloxycarbonyl and substituted benzyloxycarbonyl such as chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropyloxycarbonyl, ethoxycarbonyl, allyloxycarbonyl; (4) cycloalkyl urethan type protecting groups illustrated by cyclopentyloxycarbonyl, adamantyloxycarbonyl, cyclohexyloxycarbonyl;(5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R is tert-butyloxycarbonyl;

$R^1$ and $R^6$ are a protecting group for the sulfhydryl group on the cysteinyl amino acid residue in the undecapeptide. Illustrative of $R^1$ and $R^6$ is a group selected from the class consisting of benzyl; substituted benzyl wherein the substituent is at least one of methyl, methoxy, nitro (e.g. p-methylbenzyl, p-nitrobenzyl, 2,4,6-trimethylbenzyl, etc); carboxymethyl; trityl, benzyloxycarbonyl, benzhydryl, p-methoxybenzyloxycarbonyl, benzylthiomethyl, ethylcarbamyl, thioethyl, tetrahydropyranyl, acetamidomethyl, benzoyl, s-sulfonate salt, etc.

$R^2$ is a protecting group for the side chain amino substituent of lysine or $R^2$ is hydrogen which means there is no protecting group on the side chain amino substituent. Illustrative of suitable side chain amino protecting groups are benzyloxycarbonyl and substituted benzyloxycarbonyl said substituent being selected from halo (e.g. chloro, bromo, fluoro) and nitro (e.g. 2-chlorobenzyloxycarbonyl, p-nitro benzyloxycarbonyl, 3,4-dichlorobenzyloxycarbonyl), tosyl, t-amyloxycarbonyl, t-butyloxycarbonyl, diisopropylmethoxycarbonyl etc. The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group should not be the same.

$R^3$, $R^4$ and $R^5$ are protecting groups for the alcoholic hydroxyl group of threonine and serine and is selected from the class consisting of acetyl, benzoyl, tert-butyl, trityl, benzyl, 2,6 dichlorobenzyl and benzyloxycarbonyl. The preferred protecting group is benzyl; or $R^3$, and/or $R^4$ and/or $R^5$ is hydrogen which means there is no protecting group on the alcoholic hydroxyl function.

$R^7$ is α-carboxyl protecting group which is stable under the process conditions used to remove the α-amino protecting group until the peptide of the desired chain length has been formed. Illustrative of $R^7$ is a group selected from the class consisting of $C_1$-$C_6$ alkyl (e.g. methyl, ethyl, butyl, pentyl, isobutyl, etc); benzyl; substituted benzyl wherein the substituent is selected from at least one of nitro, methoxy and methyl (e.g. p-methoxybenzyl, p-nitrobenzyl, 2,4-dimethoxybenzyl, 2,4,6-trimethylbenzyl, pentamethylbenzyl), phenacyl, phthalimidomethyl, β-methylthioethyl, 4-picolyl and 4-(methylthio)phenyl. Preferably $R^7$ is $C_1$-$C_6$ alkyl, benzyl or substituted benzyl.

In selecting a particular $R^1$, $R^2$, $R^3$, $R^4$, $R^5$ and $R^6$ side chain protecting group to be used in the synthesis of the peptides of formula (III), the following rules should be followed: (a) the protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The undecapeptides of formulas I through III are prepared in accordance with the reaction scheme shown in the flow diagram appended hereto. With reference to the flow diagram, the decapeptide (A), representing R—Asn—Phe—Phe—Trp—Lys($R^2$)—Thr—($R^3$)—Phe—Thr($R^4$)—Ser($R^5$)—Cys($R^6$)—$OR^7$ which Trp is L-tryptophyl, is obtained by the process described in copending application Ser. No. 376,472, now U.S. Pat. No. 3,862,925, the disclosure of which is incorporated by reference, or its D-trp analogue, prepared in the same manner as the L-Trp compound by substituting D-Trp for L-Trp in the coupling sequence, is treated with a reagent that will remove the α-amino protecting group from the asparaginyl amino acid residue to yield H—Asn—Phe—Phe—Trp—Lys(R-$^2$)—Thr($R^3$)—Phe—Thr($R^4$)—Ser($R^5$)—Cys(R-$^6$)—$OR^7$ (B) where Trp is of the L or D configuration. The cleaving reagent is one which will remove the α-amino protecting group without cleavage of the side chain protecting groups. A particular suitable reagent is trifluoroacetic acid which will cleave tert-butyloxycarbonyl off the α-amino group but not benzyl or benzyloxycarbonyl side chain protecting groups. Other standard cleaving reagents are described by Schroder and Lubke, supra, pp 72–74.

The decapeptide of formula (B) is then coupled with R-Cys($R^1$)—OH (C), after the free carboxyl group of formula (C) has been activated with a suitable carboxylic acid activating reagent to form the undecapeptide R—Cys($R^1$)—Asn—Phe—Phe—Trp—Lys($R^2$)—Thr—($R^3$)—Phe—Thr($R^4$)—Ser($R^5$)—Cys($R^6$)—$OR^7$ (D) where Trp is of the L or D configuration. The compound of formula (B), which is preferably in the form of a salt, may be present in the reaction medium while the carboxyl group activated derivative of formula (C) is being formed or it may be added to the reaction vessel after the activated compound has been formed. The coupling is carried out at a temperature between about +30° C. and −30° C. in the presence of an inert organic solvent such as dichloromethane, acetonitrile, dimethylformamide, chloroform, dioxane, toluene, methylene chloride, etc. If the compound of Formula (B) is added to the reaction medium as an acid addition salt, an acid acceptor is included in the reaction medium so that a free base is formed in situ which reacts with the activated derivative of a compound of Formula C. Suitable acid acceptors include tertiary amines (e.g. triethylamine, pyridine, quinoline, dimethylaniline, etc.) alkali metal carbonates or other acid binding agents known in the art.

The activating reagents used in the aforedescribed synthesis are those well known in the peptides art. Illustrative of these are: (1) carbodiimides (e.g. $N,N^1$-dicyclohexylcarbodiimide, N-ethyl $N^1$-(γ-dimethylamino propyl carbodiimide); (2) cyanamides (e.g. N,N-dibenzylcyanamide; (3) ketenimines; (4) isoxazolium salts (e.g. N-ethyl-5-phenyl isoxazolium-3$^1$-sulfonate; (5) monocyclic nitrogen containing heterocyclic amides of aromatic character containing one through four nitrogens in the ring such as imidazolides, pyrazolides, 1,2,4-triazolides. Specific heterocyclic amides that are useful include $N,N^1$-carbonyl diimidazole, $N,N^1$-carbonyl-di-1,2,4-triazole; (6) alkoxylated acetylene (e.g. ethoxyacetylene); (7) reagents which form a mixed anhydride with the carboxyl moiety of the amino acid (e.g. ethylchloroformate, isobutylchloroformate) and (8) nitro-containing heterocyclic compounds having a hydroxy group on one ring nitrogen (e.g. N-hydroxyphthalimide, N-hydroxysuccinimide, N-hydroxybenzotriazole). Other activating reagents and their use in peptide coupling are described by Schroeder and Lubke supra, in Chapter III and by Kapoor, J. Pharm. Sci., 59, pp 1–27, (1970).

A particular suitable activating system for a compound of formula (C) is the use of the combination of $N,N^1$-dicyclohexylcarbodiimide (DCC) and N-hydroxybenzotriazole which minimizes recemization.

Following the formation of the undecapeptide of formula (D), the side chain protecting groups $R^1$, $R^2$, $R^3$, $R^4$, $R^5$ and $R^6$ and the α-amino protecting group R are cleaved and the ester function $OR^7$ is converted to the free acid to obtain a undecapeptide of formula (II). The cleavage of the side chain protecting groups, α-amino protecting group and formation of the free acid may be accomplished in a single step or may be performed stepwise depending on the selection of the cleaving reagent. A particular suitable reagent is liquid hydrogen fluoride. If desired trifluoroacetic acid can be used to remove the α-amino protecting group following by hydrogenation over a palladium catalyst to split off such side chain protecting groups as benzyl and benzyloxycarbonyl, or sodium in liquid ammonia may be used.

The compound of formula (II) is converted to a compound of formula (I) by air oxidation, preferably by surface oxidation as described in Example 2 herein.

The following examples are illustrative of the preparation of the compounds of formulas I through III.

EXAMPLE 1

N-tert-Butyloxycarbonyl-S-p-methoxybenzyl-L-cysteinyl-L-asparaginyl-L-phenylalanyl-L-phenylalanyl-L-tryptophyl-N -benzyloxycarbonyl-L-lysyl-O-benzyl-L-threonyl-L-phenylalanyl-O-benzyl-L-threonyl-O-benzyl-L-seryl-S-p-methoxybenzyl-L-cysteine benzyl ester N-t-Butyloxycarbonyl-L-asparaginyl-L-phenylalanyl-L-phenylalanyl-L-tryptophyl-N -benzyloxycarbonyl-L-lysyl-O-Benzyl-L-threonyl-L-phenylalanyl-O-Benzyl- L-threonyl-O-Benzyl-L-seryl-S-p-Methoxybenzyl-L-cysteine Benzyl Ester (2.3 g., 1.15 m moles) prepared as described in Example XI of U.S. Pat. No. 3,862,925, is mixed with anisole (4 ml.) and treated with trifluoroacetic acid (75 ml.) for 1 hour at room temperature. The excess trifluoracetic acid is removed in vacuo and the dark residue is triturated with dry diethyl ether to give a solid, 2.2 g. (95%).

Part of the above solid (1.4 g., 0.7 m moles) is dissolved in dimethylformamide (ca. 50 ml.) and mixed with triethylamine (0.095) then cooled in an ice-bath mixed with N-tertbutyloxycarbonyl-S-p-methoxybenzyl-L-cysteine (0.341 gr.) N-hydroxybenzotriazole (0.2 g., 1.5 m moles) then treated with N,N¹-dicyclohexylcarbodiimide (0.206 gr.) for two hours in the cold and 48 hours at room temperature. The N,N¹-dicyclohexylurea which separates is filtered off and the filtrate is treated with excess water to give a solid which is washed with 5% $KHSO_4$, water, aqueous $KHCO_3$, $H_2O$. The above solid is digested with hot abs. ethanol, then reprecipitated from dimethylformamide-water to yield 1 g. (44%) of white solid having a melting point of 232–236° C.

Analysis for $C_{111}H_{130}N_{12}S_2O_{21}$ (2000.15)
Calculated for: C, 66.65, H, 6.55, N, 8.40.
Found: C, 66.50, H, 6.33, N, 8.35.

EXAMPLE 2

L-Cysteinyl-L-asparaginyl-L-phenylalanyl-L-phenylalanyl-L-tryptophyl-L-lysyl-L-threonyl-L-phenylalanyl-L-threonyl-L-seryl-L-cysteine- (1,11 cyclic disulfide), diacetate salt The protected undecapeptide obtained in Example 1 (0.8 g.) is mixed with 6 ml. anisole and treated with anhydrous liquid hydrogen fluoride (100 ml) at 20° C. for 30 minutes. The hydrogen fluoride is evaporated as fast as possible (ca. 1 hour) and the residue is taken in 10% aq. acetic acid containing 0.1% mercaptoethanol and washed with diethyl ether (free of oxygen and peroxides). The aqueous layer is lyophilized to yield a fluffy solid (0.54 g.) which is L-cysteinyl-L-asparaginyl-L-phenylalanyl-L-phenylalanyl-L-tryptophyl-L-lysyl-L-threonyl-L-phenylalany-L-threonyl-L-seryl-L-cysteine diacetate (compound of formula II). This solid (0.357 g.) is dissolved in 1500 ml. water (flushed with hydrogen) then the pH is adjusted to 7.8 with dilute $NH_4OH$ and left to stand in the open air for 3 days and then lyophilized twice. The crude product (184 mg.) is dissolved in the upper phase of a mixture of n-butanol-water-glacial acetic acid (4:5:1, v/v) and applied onto a column (2.5 × 60 cm.) of Sephadex G-25 (fine) which is equilibrated first with the lower aqueous phase of the above mixture, then with the upper phase. Fractions of 2 ml. volume are collected on elution with the upper phase and the desired compound emerges between fraction number 72-93. Lyophilization gives a fluffy white solid, 41 mg. $R_f$ (n-butanol-water-acetic acid 4:5:1, v/v) 0.45; $R_f$ (i-amyl alcohol-water-pyridine, 7:6:7, v/v) 0.65 (cellulose covered plates, Ehrlich spray). Amino acid analysis: Asp (1) 1.01; Thr (2) 2.09; Ser (1) 0.80; Cys (2) 1.60; Phe (3) 3; Lys (1) 0.94; Trp (not determined).

To illustrate the solid phase synthesis of the undecapeptides of this invention, the following example is provided. Although the D-tryptophyl[8] derivative is specifically prepared, the corresponding L-tryptophyl[8] containing analogue is preparable by the same technique.

EXAMPLE 3

N-tert-Butyloxycarbonyl-S-p-methoxybenzyl-L-cysteinyl-L-asparaginyl-L-phenylalanyl-L-phenylalanyl-D-tryptophyl-ε-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl polystyrene Chloromethylated polystyrene (Lab. Systems Inc.) was esterfied with BOC-Cys(SMBZL)OH according to Gisin, Helv. Chem. Acta., 56 1976(1973). The polystyrene resin ester was treated according to schedule A for the incorporation of Boc-Ser(Bzl)OH BOC-Thr(Bzl)OH, BOC-Phe OH, BOC-Thr(Bzl)OH, BOC-Lys(ClZ)OH, BOC-D-Trp OH, BOC-Phe OH, BOC-Phe OH, BOC-Asn OH, BOC-Cys(SMBZL)OH to afford the title peptido-resin Schedule A:
1. Wash with $CH_2Cl_2$ X 3
2. Treat with TFA-$CH_2Cl_2$-EDT(1:1:4%) for 5 minutes
3. Repeat 2 for 25 minutes
4. Wash with $CH_2Cl_2$ × 3
5. Wash with DMF
6. Treat with 12% TEA in DMF twice for 3 minutes
7. Wash with DMF
8. Wash with $CH_2Cl_2$ × 3
9. Treat with 4 equivalents of the corresponding amino acid derivative in $CH_2Cl_2$-DMF and 4 equivalents of N-hydroxybenzotriazole and stir for 5 minutes
10. Add in two portions 5 equivalents of DIC dissolved in $CH_2Cl_2$ and over a period of 30 minutes reaction time 12–18 hours.
11. Wash with DMF × 3
12. Wash with $CH_2Cl_2$ × 3
13. Test ninhydrin reaction accordings to Kaiser et al. Annal. Biochem. 34 595(1970) In case of incomplete reaction repeat lines 9 to 13 as above.

During the addition of BOC-Asn-OH a two-fold quantity of N-hydroxybenzotriazole over the normal, i.e. 8 equivalents, was added.

Amino acid analysis, Asp(1)1.2 Thr(2)2.02 Ser(1)0.53 Cys(2)1.78 Phe(3)3 Lys(1)1.05 $NH_3$(1)2.23 Trp N.D.

EXAMPLE 4

L-Cysteinyl-L-asparaginyl-L-phenylalanyl-L-phenylalanyl-D-trypto-phyl-L-lysyl-L-threonyl-L-phenylalanyl-L-threonyl-L-seryl-L-cysteine(1-11 disulfide)

The peptido resin of the previous example (20.5 g.) was mixed with 20 ml. anisole and treated with liquid HF for 40 minutes at 0° C. The excess HF was removed in vacuo and the residue was extracted with dil. AcOH. The aqueous extract was lyophilized to afford 3.45 g. of white solid. This solid was oxidized as described for the L-tryptophyl containing peptide and purified in a similar manner to give the title compound, 26 mg. $R_f$ (n-Butanol-water-acetic acid) 0.54. $R_f$ (n-butanol-water-acetic acid-pyridine)0.68.

Amino acid analysis: Asp(1)0.99 Thr(2)2.41 Ser(1)1.05 Cys(2)2.18 Phe(3)2.80 Lys(1)1 $NH_3$(1)0.33 Trp N.D.

The growth hormone activity of the compound of Example 2 was determined by injecting rats weighing about 150 g. first with nembutal intraperitoneally at a dose of 50 mg/kg then after 5 minutes injecting the rats subcutaneously with a solution of the compound of Example 2 in saline at a dose of 100 m.g. per rat. Blood samples are taken 15 minutes after injection with the compound of Example 2 and the growth hormone level determined by radioimmunoassay. The average growth hormone level in the control rats (9 animals) was found to be 212±26 ng/ml whereas the growth hormone level in the rats (10 animals) given the compound of Example 2 was found to be 103±13 ng/ml.

The activity of the product of Example 3 was determined by the same technique as the compound of Example 2. The dose given the test animals was 1 mg/kg. Growth hormone concentration was reduced to 28±4 ng/ml from the control level of 75±16 (p<0.01). The insulin concentration in micro units per milliliter was reduced marginally to 168±13 from the control level of 208±11 (p>0.05). The glucagon concentration in pico grams per milliliter was not effected, being 31±3 in the treated animals as opposed to 37±2 in the control animals.

The compounds of formula I described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as juvenile diabetes and acromegaly. The contemplated dose range for oral administration in tablet or capsule form to large mammals is about 0.015 mg to about 7 mg/kg of body weight per day while the dose range for intravenous injection is an aqueous solution is about 1.14 µg to about 0.15 mg/kg of body weight per day. When administered subcutaneously or intramuscularly a dose range of about 1.5 µg to about 7 mg/kg of body weight per day is contemplated. Obviously, the required dosage will vary with the particular condition being treated, the severity of the condition and the duration of treatment. If the active ingredient is administered in tablet form the tablet may contain: a binder such as gum tragacanth, corn starch, gelatin, an excipient such as dicalcium phosphate; a disintegrating agent such as corn starch, alginic acid, etc.; a lubricant such as magnesium stearate; and a sweetening and/or flavoring agent such as sucrose, lactose, wintergreen, etc. Suitable liquid carriers for intravenous administration include isotonic saline, phosphate buffer solutions, etc.

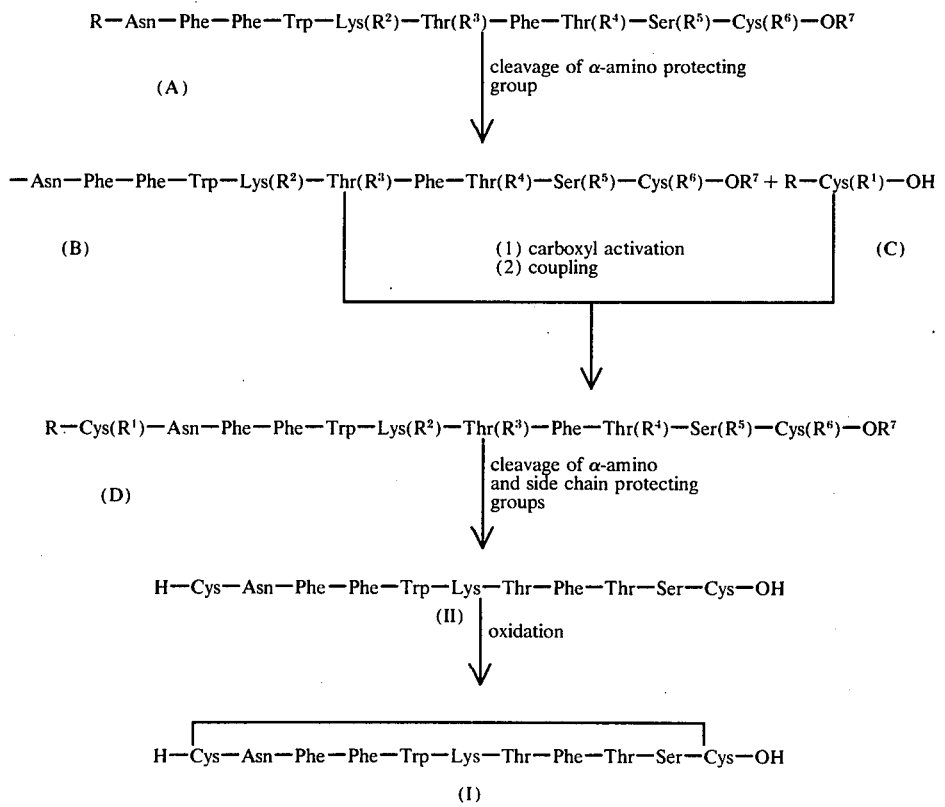

FLOW DIAGRAM

What is claimed is:

1. A undecapeptide selected from those of the formula

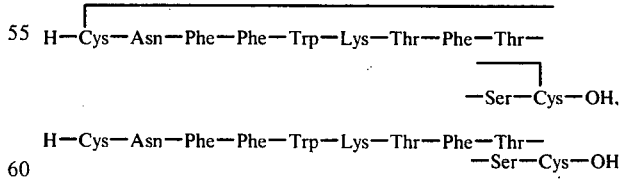

and the non-toxic acid addition salts thereof, in which Trp is L-tryptophyl or D-tryptophyl and all other amino acid residues in said undecapeptide having an asymmetric α-carbon atom being of the L-configuration.

2. A peptide according to claim 1 which is: L-Cysteinyl-L-asparaginyl-L-phenylalanyl-L-phenylalanyl-L-tryptophyl-L-lysyl-L-threonyl-L-phenylalanyl-L-threonyl-L-seryl-L-cysteine and a non-toxic acid addition salt thereof.

3. A peptide according to claim 1 which is: L-Cysteinyl-L-asparaginyl-L-phenylalanyl-L-phenylalanyl-D-tryptophyl-L-lysyl-L-threonyl-L-phenylalanyl-L-threonyl-L-seryl-L-cysteine and a non-toxic acid addition salt thereof.

4. A peptide according to claim 1 which is: L-Cysteinyl-L-asparaginyl-L-phenylalanyl-L-phenylalanyl-L-tryptophyl-L-lysyl-L-threonyl-L-phenylalanyl-L-threonyl-L-seryl-L-cysteine (cyclic 1,11 disulfide) and a non-toxic acid addition salt thereof.

5. A peptide according to claim 1 which is: L-Cysteinyl-L-asparaginyl-L-phenylalanyl-L-phenylalanyl-D-tryptophyl-L-lysyl-L-threonyl-L-phenylalanyl-L-threonyl-L-seryl-L-cysteine (cyclic 1,11 disulfide) and a non-toxic acid addition salt thereof 6. A undecapeptide of the formula:

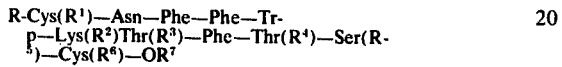

wherein:

Trp is L-tryptophyl or D-tryptophyl;

R is selected from the group consisting of hydrogen or an α-amino protecting group;

$R^1$ and $R^6$ are protecting groups for the sulfhydryl group on the cysteinyl amino acid residue selected from the group consisting of benzyl, trityl, benzyloxycarbonyl, benzhydryl, tetrahydropyranyl, acetamidomethyl, benzoyl, benzylthiomethyl, ethylcarbamyl, thioethyl, p-methoxybenzyloxycarbonyl, s-sulfonate salt and substituted benzyl wherein said substituent is selected from the group consisting of methyl, methoxy and nitro;

$R^2$ is selected from the group consisting of hydrogen and a protecting group for the side chain amino substituent of the lysine residue selected from tosyl, t-amyloxycarbonyl, t-butyloxycarbonyl, diisopropyloxycarbonyl, benzyloxycarbonyl and substituted benzyloxycarbonyl wherein said substituent is selected from the class consisting of halo and nitro;

$R^3$, $R^4$ and $R^5$ are selected from the group consisting of hydrogen and a protecting group for the alcoholic hydroxyl group of the threonine and serine residues selected from acetyl, benzoyl, tert-butyl, trityl, benzyl, 2,6 dichlorobenzyl and benzyloxycarbonyl; and $R^7$ is a α-carboxyl protecting group selected from the class consisting of $C_1$-$C_6$ alkyl, benzyl, substituted benzyl, phenacyl, phthalimidomethyl, 3-methylthioethyl, 4-picolyl and 4-(methylthio) phenyl, said substituent on benzyl being selected from at least one of methyl, methoxy and nitro; and the acid addition salts thereof, all other amino acid residues in said undecapeptide having an asymmetric α-carbon atom being of the L-configuration.

7. A compound according to claim 4 wherein R is tert-butyloxycarbonyl.

8. A compound according to claim 5 wherein: $R^1$ and $R^6$ is p-methoxybenzyl; $R^2$ is benzyloxycarbonyl; $R^3$, $R^4$ and $R^5$ are each benzyl and $R^7$ is benzyl.

* * * * *